US006537533B2

(12) United States Patent
Alvarado

(10) Patent No.: US 6,537,533 B2
(45) Date of Patent: Mar. 25, 2003

(54) HAIR CONDITIONER COMPOSITION THAT IS NON-IRRITATING TO THE EYES

(75) Inventor: Robert M. Alvarado, Glenview, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/771,868

(22) Filed: Jan. 29, 2001

(65) Prior Publication Data
US 2002/0143063 A1 Oct. 3, 2002

(51) Int. Cl.[7] .......................... A61K 7/00; A61K 7/075
(52) U.S. Cl. .................. 424/70.28; 424/70.22; 424/70.1; 424/70.4; 424/47
(58) Field of Search ................. 424/70.28, 70.01, 424/70.4, 70, 70.22, 47

(56) References Cited

U.S. PATENT DOCUMENTS

| 4,374,825 A | 2/1983 | Bolich, Jr. et al. |
| 4,387,090 A | 6/1983 | Bolich, Jr. |
| 4,777,039 A | 10/1988 | Lang et al. |
| 4,950,468 A | 8/1990 | Nakamura et al. |
| 4,971,786 A | 11/1990 | Grollier et al. |
| 5,213,793 A | 5/1993 | Moses et al. |
| 5,679,327 A | * 10/1997 | Darkwa et al. ............. 424/70.4 |
| 6,274,128 B1 | * 8/2001 | Bergmann et al. .......... 424/70.1 |
| 6,322,778 B1 | * 11/2001 | Parr et al. ................. 424/70.28 |

* cited by examiner

Primary Examiner—Michael G. Hartley
Assistant Examiner—M. Haghighatian
(74) Attorney, Agent, or Firm—Milton L. Honig

(57) ABSTRACT

The invention relates to hair conditioner compositions that are non-irritating to the eye and which comprise:

a) a C20–C24 quaternary ammonium compound, which has ethosulfate or methosulfate as an anion;

b) a second C20–C24 quaternary ammonium compound, which has chloride or bromide as an anion;

c) a compound which is solid at room temperature and which is selected from the group consisting of a fatty alcohol, an ester, an amine, an amide, an acid, and a water-soluble polymer;

d) optionally a compound, which is liquid at room temperature, selected from the group consisting of a water insoluble emollient, a water insoluble lubricating agent, and a water insoluble conditioning compound; and wherein a) and b) are present in a weight ratio of about 1:10 to about 10:1; are described.

1 Claim, No Drawings

HAIR CONDITIONER COMPOSITION THAT IS NON-IRRITATING TO THE EYES

BACKGROUND OF THE INVENTION

Rinse-out hair care conditioner compositions are typically used by contacting the hair with the hair care conditioner, working the conditioner into the hair, and then rinsing the conditioner from the hair. In the rinsing step it is possible for some of the conditioner composition to get into the eyes. Because conditioning agents that are traditionally used in conditioner compositions can be harsh and can cause tear formation, the rinsing step can cause discomfort to the consumer. For this reason, it would be desirable to provide hair care conditioner compositions that are non-irritating to the eyes. Compositions with such a property would be desirable for all consumers, and would be especially desirable for children who often cannot easily tolerate the eye irritation caused by traditional conditioner compositions.

The present invention provides effective hair conditioner compositions which are non-irritating to the eyes.

Publications and products which relate to the field of the invention are as follows:

Helene Curtis Japan Program Conditioner;

L'Oreal for Kids Conditioner;

U.S. Pat. No. 4,374,825 discloses hair conditioner compositions in the form of an emulsion comprising a volatile agent, a nonionic, water soluble thickening agent, a cationic hair conditioning agent and water.

U.S. Pat. No. 4,777,039 discloses a pearlescent hair conditioner composition based on a quaternary compound and a fatty alcohol, consisting of (A) 0.2 to 10 percent by weight of coconut fatty acid monoethanolamide, (B) 0.4 to 10 percent by weight of a straight-chain fatty alcohol with m carbon atoms (m=14 to 18), (C) 0.1 to 4 percent by weight of a quaternary compound of a specified formula (D) 70 to 99.3 percent by weight water and (E) 0 to 24 percent by weight of conventional cosmetic added substances.

U.S. Pat. No. 4,387,090 discloses hair conditioner compositions containing a volatile, liquid hair conditioning agent, which agent is thickened with a hydrophobic thickener.

U.S. Pat. No. 4,950,468 discloses a hair treating composition having excellent resistance to washing which comprises a dimethyl silicone rubber and a quaternary ammonium salt ingredient consisting of stearyltrimethylammonium chloride and behenyltrimethylammonium chloride.

U.S. Pat. No. 4,971,786 discloses a cosmetic composition for the treatment and care of the hair, containing, in a cosmetically acceptable medium: at least one cationic surfactant agent of a specified formula; at least one quaternized hydroxyalkylcellulose polymer; and at least one ethoxylated copolymer of dimethylsiloxane/3-hydroxypropylmethylsiloxane.

U.S. Pat. No. 5,213,793 discloses a water-in-oil emulsion hair conditioner composition containing no more than about one percent total solids, and at least one cationic hair conditioning agent, the hair conditioner composition preferably comprising from about five to about ten percent of a volatile oil, up to about three percent of a hydrophobic emulsifying agent, from about 0.01% to about 0.5% of the cationic hair conditioning agent, and water.

SUMMARY OF THE INVENTION

The invention relates to aqueous hair conditioner compositions that are non-irritating to the eye and which comprise:

a) a C20–C24 quaternary ammonium compound, which has ethosulfate or methosulfate or mixtures thereof as an anion;

b) a second C20–C24 quaternary ammonium compound, which has chloride or bromide or mixtures thereof as an anion;

c) a compound which is solid at room temperature and which is selected from the group consisting of a fatty alcohol, an ester, an amine, an amide, an acid, and a water-soluble polymer;

d) optionally a compound, which is liquid at room temperature, selected from the group consisting of a water insoluble emollient, a water insoluble lubricating agent, and a water insoluble conditioning compound; and wherein a) and b) are present in a weight ratio of about 1:10 to about 10:1.

The invention also relates to a process for preparing a composition of the invention.

The invention also relates to a method for conditioning hair which comprises contacting said hair with a composition of the invention.

DETAILED DESCRIPTION OF THE INVENTION

As used herein % means weight % of the total composition unless otherwise specified. Degrees are in degrees Celsius unless otherwise specified. "Non-irritating to the eye" means little or no discomfort to the human eye. A "C20–C24 quaternary ammonium compound", means a quaternary ammonium compound which has at least one saturated or unsaturated, straight-chain, or branched chain hydrocarbon substituent that has about 20 to about 24 carbon atoms.

The invention relates to aqueous hair conditioner compositions that are non-irritating to the eye and which comprise:

a) a C20–C24 quaternary ammonium compound, which has ethosulfate or methosulfate or mixtures thereof, as an anion;

b) a second C20–C24 quaternary ammonium compound, which has chloride or bromide or mixtures thereof, as an anion;

c) a compound, which is a solid at room temperature, selected from the group consisting of a solid fatty alcohol, an ester, an amine, an amide, an acid, and a water-soluble polymer;

d) optionally a compound, which is liquid at room temperature, selected from the group consisting of a water insoluble emollient, a lubricating agent, and a conditioning compound; and wherein a) and b) are present in a weight ratio of about 1:10 to about 10:1.

More preferably, compositions of the invention can comprise:

a) about 0.1 to about 3% of a C20–C24 quaternary ammonium compound, which has ethosulfate or methosulfate or mixtures thereof as an anion;

b) about 0.1 to about 3% of a second C20–C24 or mixtures thereof quaternary ammonium compound, which has chloride or bromide as an anion;

c) about 0.1 to about 5% of a compound which is solid at room temperature and which is selected from the group consisting of a solid fatty alcohol having about 16 to about 24 carbon atoms, an ester, an amine, an amide, an acid, and a water-soluble polymer; and d) optionally a compound, which is liquid at room temperature, selected from the group consisting of a water insoluble emollient, a lubricating agent, and a conditioning compound; and wherein a) and b) are present in a weight ratio of about 1:10 to about 10:1.

The invention also relates to hair conditioner compositions as described above wherein a) and b) taken together are preferably present in said compositions in an amount of about 0.1% to about 5%.

The invention also relates to hair conditioner compositions as described above wherein c) is preferably present at from about 0.1% to about 5%.

The invention also relates to hair conditioner compositions as described above wherein c) is preferably present at from 0.1% to about 5% and is preferably at least one solid fatty alcohol or a water-soluble polymer.

Compositions of the invention are in the form of rinse-out conditioners, and may take the form of a liquid, lotion, mousse, cream, or aerosol product. As noted above, compositions of the invention are formulated so as to cause little or no irritation to the eye. Compositions of the invention are also esthetically pleasing.

What follows is a description of the ingredients used in the compositions of the invention.

C20–C24 Quaternary Ammonium Compounds

The compositions of the invention comprise at least two C20–C24 quaternary ammonium compounds. One such compound has ethosulfate or methosulfate or mixtures thereof as an anion. The other quaternary ammonium compound has bromide or chloride or mixtures thereof as an anion. The weight ratio of the first quaternary ammonium compound to the second quaternary ammonium compound is about 1:10 to about 10:1.

It has unexpectedly been found that the use of at least one C20–C24 quaternary ammonium compound which has ethosulfate or methosulfate or mixtures thereof, as an anion; in combination with at least one other quaternary ammonium compound which has bromide or chloride or mixtures thereof as an anion; results in hair care conditioner compositions which provide the same conditioning benefit as compositions which have only one quaternary ammonium compound. As a result the compositions of the invention have lower irritancy to the eyes. While any C20–C24 quaternary ammonium compound with the appropriate anions may be used in he compositions of the invention, listed below are non-limiting examples of behenyl-substituted quaternary ammonium compounds which may be used in compositions of the claimed invention. It will be understood that any individual hair conditioner composition of the invention can comprise a mixture of two or more of such more behenyl quaternary ammonium compounds. As noted above, such mixtures afford a high conditioning benefit along with low irritancy to the eyes.

Compositions of the invention can include mixtures of behentrimonium methosulfate, behentrimonium chloride; behenamidopropyl PG-dimonium chloride, behenalkonium chloride, behenoyl PG-trimonium chloride; behenamidopropyl ethyldimonium ethosulfate, C18–C24 isoalkylamidopropylethyldimonium ethosulfate, dibehenyl/diarachidyl dimonium chloride, dibehenyldimonium chloride.

The compositions of the invention may contain fatty alcohols, esters, amines, amides, and acids, which are solid at room temperature (25° C.), as well as water-soluble anionic, cationic, and nonionic polymers.

Fatty alcohols are higher molecular weight nonvolatile alcohols. They can be produced from fatty acids by reduction of the fatty acid COOH— grouping to the hydroxyl function. Alternatively, several completely synthetic routes yield fatty alcohols which may be structurally identical or similar to the nature-derived alcohols. Fatty alcohols generally are primary alcohols conforming to the structure $RCH_2OH$; those fatty alcohols prepared from naturally occurring fatty acids normally contain an even number of carbon atoms. Fatty alcohols may be used as emollients in compositions of the invention. They are valuable as co-emulsifiers and are employed to increase the viscosity of emulsions, shampoos, and other products. Fatty alcohols would include alcohols having about C16 to about C24 fatty alcohols.

The following list of fatty alcohols which may be used in compositions of the invention is meant to be illustrative and not limiting. These fatty alcohols include a fatty alcohol or fatty acid, or derivative thereof, or a mixture of any of these having a chain length of from about 8 to about 36 carbon atoms. More preferably from about 12 to about 22 carbon atoms. These materials may be predominantly linear or may be branched. Preferred are stearyl alcohol, cetyl alcohol, behenyl alcohol, lauryl alcohol, myristyl alcohol, and coco alcohol.

Esters included here as ingredients in compositions of the invention include esters that are also classified as glyceryl esters, i.e., glyceryl distearate, glycol esters, i.e., glycol distearate, and fatty alkyl acid esters, i.e., cetyl palmitate.

Amines are the organic substitution compounds of ammonia, and can carry from 1 to 4 organic substituents. The amine salts may also be included in the composition of the invention. Alkoxylated amines, including quaternary alkoxylated amines, alkylamido alkylamines, i.e., stearamidopropyl dimethylamine, and there salts may also be used.

Amides are hydrolyzable derivatives of carboxylic acids and are prepared via a number of synthetic and biological routes. Amides may be used as moisturizers in compositions of the invention. Alkanolamides, i.e., cocamide MEA, alkoxylated amides, i.e., PEG-5 Cocamide, and their salts can also be used.

Acids refer to alkoxylated carboxylic acids, alkyl-substituted amino acids, carboxylic acids, and fatty acids. Alkoxylated carboxylic acids serve as emollients, emulsifiers, solubilizers, and suspending agents in compositions of the invention. Alkyl-substituted amino acids can also be used in compositions of the invention. Fatty acids are a common source of raw materials for the synthesis of cosmetic ingredients. They are used in compositions of the invention. They are frequently as salts which are formed in situ from the acid and a suitable alkali. Examples of these types of acids are stearic acid, palmitic acid, citric acid, and lactic acid.

Water-soluble polymers which can be included in compositions of the invention can include either naturally derived or synthetic polymers. These polymers can also be quaternized. Naturally derived polymers include those derived from cellulose and guar, e.g., hydroxyethyl cellulose and guar hydroxypropyltrimonium chloride. Synthetic polymers can be acrylate polymers and carbomers, e.g., Polyquaternium 7, Polyquaternium-10, Polyquaternium-11, and acrylamidopropyltrimonium chloride/acrylamide copolymer.

Optional Ingredients

Optional ingredients which can be included in compositions of the invention are described below.

Water Insoluble Emollients and Other Compounds

Water insoluble materials such as emollients and/or lubricating agents/conditioning compounds such as silicones and silicone derivatives, esters, amides, amines, hydrocarbons, and alcohols may also be included in this composition.

Listed below are non-limiting examples of water insoluble emollients and/or lubricating agents/conditioning compounds such as silicones and silicone derivatives, esters, amides, amines and alcohols, which are liquids at room temperature (about 25° C), which may be included in compositions of the invention.

Silicones, such as organo-substituted polysiloxanes, are linear or cyclic polymers of monomeric silicon/oxygen monomers. Linear silicones, cyclic silicones, functionally substituted silicones, dimethicone copolyol, and silanes may be included in the compositions of the invention.

Esters included here as optional ingredients include esters that are also classified as glyceryl esters, i.e., caprylic/capric triglyceride, and fatty acid esters, i.e., sorbitan oleates and C12–C15 benzoates.

Amides are hydrolyzable derivatives of carboxylic acids and are prepared via a number of synthetic and biological routes. Amides may be used in the compositions of the invention as moisturizers. Alkanolamides, alkoxylated amides and their salts can also be used, e.g., linoleamide and oleamide.

Hydrocarbons are the group of compounds containing only carbon and hydrogen. Hydrocarbons are generally derived from petrochemicals, but some of them are found in the plant or animal kingdom (e.g., squalene). Their structures can vary widely, and include aliphatic, alicyclic, and aromatic compounds. Typical hydrocarbons are petrolatum, paraffin, and mineral oil, all of which can be used as emollients in compositions of the invention. Furthermore, this includes a group of hydrocarbons known as Permethyls and includes Isoeicosane, Isodocane, Isohexadecane and Polyisobutene.

Alcohols are organic compounds in which a hydroxyl group (—OH) is attached to a saturated carbon atom. Alcohols have the general formula ROH, where R may be aliphatic or alicyclic and may include aromatic rings. Polyols, phenols and glycols are also alcohols. Alcohols can be included in compositions of the invention.

As further optional components for inclusion in the compositions of the invention, the following may be mentioned: pH adjusting agents, viscosity modifiers, cosmetic fillers such as talc, kaolin; pearlescers, opacifiers, suspending agents, preservatives, coloring agents, dyes, proteins, herb and plant extracts, polyols and other moisturizing agents.

Methods of Using Hair Conditioner Compositions of the Invention

Compositions of the invention may be used as hair conditioners by contacting the hair with said compositions. The compositions are worked into the hair, usually with the fingers, and then rinsed out with water.

Compositions of the invention may be applied before or after the application of water. Compositions of the invention may be used simultaneously with water. Compositions of the invention are often applied to hair which is wet because it has just been shampooed and rinsed.

The following compositions of the invention were made and are meant to be illustrative and not limiting.

EXAMPLE 1

Composition of the Invention

| Item # | Description | Actual Wt % |
|---|---|---|
| 1 | Soft water | 93.09 |
| 2 | Behentrimonium methosulfate | 0.625 |
|   | (and) cetearyl alcohol | 1.875 |
| 3 | Behentrimonium chloride | 0.625 |
|   | (and) isopropyl alcohol | 0.125 |
| 4 | Stearyl alcohol | 0.75 |
|   | (and) ceteareth-20 | 0.25 |
| 5 | Disodium EDTA | 0.10 |
| 6 | Amodimethicone | 0.51 |
|   | (and) cetrimonium chloride | 0.12 |
|   | (and) trideceth-12 | 0.03 |
| 7 | Cyclopentasiloxane | 1.25 |
| 8 | Methylchloroisothiazolinone (and) Methylisothiazolinone | 0.05 |
| 9 | DMDM hydantoin | 0.1 |
| 10 | Fragrance | 0.5 |

In the table above, Behentrimonium methosulfate and cetearyl alcohol each has its separate weight % given; however, they are mixed together and they are listed together as item 2.

Items 3, 4, 6, and 8 are also mixtures prior to their inclusion in compositions of the invention. Items which are mixtures prior to their inclusion in the final composition are also shown in the remaining examples as well.

Manufacturing Steps

1. Item 1 is heated to 180–185° F.; item 2 is added and mixed until dissolved; item 3 is added and mixed until dissolved, and item 4 is added and mixed until dissolved.
2. The batch continues to mix and the temperature is kept constant at 180–185 F. for a minimum of 30 minutes, or until no particles are present.
3. Cooling is begun. When the batch reaches 140° F., a premix of item #5 dissolved in hot water is added to the batch and mixed at constant temperature until no particles are present.
4. At 110 F. or below, all remaining items are sequentially added to the batch, and mixed until completely homogeneous.
5. The optimal pH range is about 4.5 to about 5.5. If necessary, potassium hydroxide may be added to raise the pH into range. Also if necessary, citric acid may be added to lower the pH into the optimal range.

EXAMPLE 2

Composition of the Invention

| Item # | Description | Actual Wt % |
|---|---|---|
| 1 | Soft water | 92.24 |
| 2 | Behenamidopropyl Ethyldimonium Ethosulfate | 0.525 |
|   | (and) stearyl alcohol | 0.975 |
| 3 | Behentrimonium chloride | 0.5 |
|   | (and) isopropyl alcohol | 0.1 |
| 4 | Stearyl alcohol | 0.75 |
|   | (and) ceteareth-20 | 0.25 |
| 5 | Stearyl Alcohol | 2.0 |
| 6 | Disodium EDTA | 0.10 |

-continued

Composition of the Invention

| Item # | Description | Actual Wt % |
|---|---|---|
| 7 | Amodimethicone | 0.51 |
|  | (and) cetrimonium chloride | 0.12 |
|  | (and) trideceth-12 | 0.03 |
| 8 | Cyclopentasiloxane | 1.25 |
| 9 | Methylchloroisothiazolinone (and) Methylisothiazolinone | 0.05 |
| 10 | DMDM hydantoin | 0.1 |
| 11 | Fragrance | 0.5 |

Manufacturing Steps

1. Item 1 is heated to 180–185° F.; item 2 is added and mixed until dissolved; item 3 is added and mixed until dissolved; item 4 is added and mixed until dissolved; and item #5 is added and mixed until dissolved.
2. The batch continues to mix and the temperature is kept constant at 180–185° F. for a minimum of 30 minutes, or until no particles are present.
3. Cooling is begun. When the batch reaches 140° F., a premix of item #6 dissolved in hot water is added to the batch and mixed at constant temperature until no particles are present.
4. At 110 F. or below, all remaining items are sequentially added to the batch, and mixed until completely homogeneous.
5. The optimal pH range is about 4.5 to about 5.5. If necessary, potassium hydroxide may be added to raise the pH into range. Also if necessary, Citric Acid may be added to lower the pH into the optimal range.

EXAMPLE 3

Composition of the Invention

| Item # | Description | Actual Wt % |
|---|---|---|
| 1 | Soft water | 92.24 |
| 2 | Behenamidopropyl Ethyldimonium Ethosulfate | 0.525 |
|  | (and) stearyl alcohol | 0.975 |
| 3 | Behentrimonium chloride | 0.5 |
|  | (and) isopropyl alcohol | 0.1 |
| 4 | Stearyl alcohol | 0.75 |
|  | (and) ceteareth-20 | 0.25 |
| 5 | Cetyl Alcohol | 1.5 |
| 6 | Disodium EDTA | 0.10 |
| 7 | Amodimethicone | 0.51 |
|  | (and) cetrimonium chloride | 0.12 |
|  | (and) trideceth-12 | 0.03 |
| 8 | Cyclopentasiloxane | 1.25 |
| 9 | Methylchloroisothiazolinone (and) Methylisothiazolinone | 0.05 |
| 10 | DMDM hydantoin | 0.1 |
| 11 | Fragrance | 0.5 |

Manufacturing Steps

1. Item 1 is heated to 180–185° F.; item 2 is added and mixed until dissolved; item 3 is added and mixed until dissolved; item 4 is added and mixed until dissolved; and item 5 is added and mixed until dissolved.
2. The batch continues to mix and the temperature is kept constant at 180–185 F. for a minimum of 30 minutes, or until no particles are present.
3. Cooling is begun. When the batch reaches 140° F., a premix of item #6 dissolved in hot water is added to the batch and mixed at constant temperature until no particles are present.
4. At 110 F. or below, all remaining items are sequentially added to the batch, and mixed until completely homogeneous.
5. The optimal pH range is about 4.5 to about 5.5. If necessary, Potassium Hydroxide may be added to raise the pH into range. Also if necessary, Citric Acid may be added to lower the pH into the optimal range.

The Hair Care Conditioner Compositions of the Invention are Non-Irritating to the Eyes Flourescein leakage assay, a test which is known in the art, involves a monolayer cell culture which mimics the tight junctions found in the cornea of the eye. In this test, which is described below, the higher the leakage of sodium flourescein through the cell culture, which is caused by a particular composition, the higher is the potential for ocular irritation, to be caused by that composition.

Fluorescein Leakage in Vitro Assay Summary

The in vitro model referred to as Fluorescein Leakage Assay is used to assess ocular irritation potential and is ideal for discriminating between or ranking the ocular mildness of products such as hair conditioners.

The fluorescein leakage assay uses a cell culture system consisting of Madin-Darby Canine Kidney (MDCK) cells. As these cells proliferate they form tight junctions analogous to those found in the outermost epithelium of human corneal tissue. The cells are grown on cell culture inserts until confluent and fed with nutrient media for a period of 7 days. Test material can then be applied neat or with varying degrees of dilution for a set length of time. The test material is rinsed off and 0.01% of sodium fluorescein applied for 30 minutes. The amount of sodium fluorescein that penetrates through the cell junctions is collected, measured and calculated as % permeability or leakage (amount of damage).

In addition, the cells can continue to be maintained for up to 5 days and the fluorescein re-applied daily to measure the degree of cell recovery.

The Fluorescein Leakage In Vitro Assay was used to compare compositions of the invention with a competitive benchmark.

Each conditioner was tested undiluted, in triplicate, applied topically to the MDCK monolayer for 30 seconds. The effect of the treatment was assessed as % Permeability of sodium fluorescein through the monolayer after initial exposure and after a 24-hr recovery period. The numbers below show the % permeability of fluorescein leakage through the cell layer.

| Examples of the invention | Description | Initial | 24 hr |
|---|---|---|---|
|  |  | % permeability | |
| 1 | Example 1 | 1.9 | 1.3 |
| 2 | Example 2 | 4.4 | 1 |
| 3 | Example 3 | 5.4 | 1 |
| Control | L'Oreal Kids Cond. | 9.2 | 1.3 |

The Fluorescein Leakage Assay provided results indicating the mild ocular irritation potential and differentiation between conditioners. Examples 1, 2 and 3 above as well as the control would be classified as mild to minimal potential ocular irritants because they caused less than 10% permeability after the initial exposure and there was complete cell recovery after 24 hrs. However, based on the initial % permeability results, it can be seen that compositions of the invention will cause little or no irritation to the eyes, especially as a compared to the Control Conditioner.

Compositions of the invention are also extra mild and cause the treated hair to be easy to detangle.

What is claimed is:

1. An aqueous hair conditioner composition which consists of:
   a) a C20–C24 quaternary ammonium compound, selected from the group consisting of behentrimonium methosulfate, behenamidopropyl ethyldimonium sulfate, and C18–C24 isoalkylamidopropyl ethyldimonium ethosulfate, mixtures thereof;
   b) a second C20–C24 quaternary ammonium compound, selected from the group consisting of behentrimonium chloride, behenamidopropyl PG-dimonium chloride, behenalkanium chloride, behenoyl PG-trimonium chloride, dibehenyl/diarachidyl dimonium chloride, dibehenyldimonium chloride, and mixtures thereof;
   c) a compound which is solid at room temperature and which is selected from the group consisting of a fatty alcohol, an ester, an amine, an amide, an acid, and a water-soluble polymer;
   d) optionally a compound, which is liquid at room temperature, selected from the group consisting of a water insoluble emollient, a water insoluble lubricating agent, and a water insoluble conditioning compound; and wherein a) and b) are present in a weight ratio of about 1:10 to about 10:1.

* * * * *